US006838460B2

(12) United States Patent
Himmelsbach et al.

(10) Patent No.: US 6,838,460 B2
(45) Date of Patent: Jan. 4, 2005

(54) SUBSTITUTED PHENYLAMIDINES MEDICAMENTS CONTAINING SAID COMPOUNDS AND METHOD FOR PRODUCTION THEREOF

(75) Inventors: Frank Himmelsbach, Mittelbiberach (DE); Brian Guth, Warthausen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 85 days.

(21) Appl. No.: 10/181,576

(22) PCT Filed: Jan. 13, 2001

(86) PCT No.: PCT/EP01/00372

§ 371 (c)(1),
(2), (4) Date: Oct. 21, 2002

(87) PCT Pub. No.: WO01/53280

PCT Pub. Date: Jul. 26, 2001

(65) Prior Publication Data

US 2003/0096824 A1 May 22, 2003

(30) Foreign Application Priority Data

Jan. 21, 2000 (DE) .......................... 100 02 510

(51) Int. Cl.$^7$ ................................ A01N 61/00
(52) U.S. Cl. .................. 514/252.12; 544/400
(58) Field of Search ............... 514/252.12; 544/400

(56) References Cited

U.S. PATENT DOCUMENTS 5,958,952 A   9/1999   Himmelsbach et al.

FOREIGN PATENT DOCUMENTS

| WO | WO 96/33970 A1 | 10/1996 |
|----|----------------|---------|
| WO | WO 00 05207 A1 | 2/2000  |

*Primary Examiner*—Deepak Rao
*Assistant Examiner*—Zachary C. Tucker
(74) *Attorney, Agent, or Firm*—Robert Raymond; Michael Morris; Philip I. Datlow

(57) ABSTRACT

The present invention relates to phenylamidines of general formula (I)

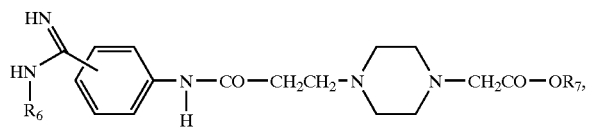

wherein $R_6$ and $R_7$ are defined as in claim 1, the tautomers, the stereoisomers including mixtures thereof and the salts thereof, particularly their physiologically acceptable salts with inorganic or organic acids or bases, which have valuable pharmacological properties, preferably antithrombotic effects, pharmaceutical compositions containing these compounds, their use and processes for preparing them.

8 Claims, No Drawings

SUBSTITUTED PHENYLAMIDINES MEDICAMENTS CONTAINING SAID COMPOUNDS AND METHOD FOR PRODUCTION THEREOF

This application was filed under 35 U.S.C. 371, and is the U.S. National Stage of PCT/EP01/00372, filed Jan. 13, 2001.

The scope of protection of WO 96/33970 covers phenylamidines of general formula

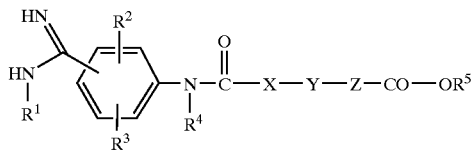

wherein $R^1$ denotes inter alia a $C_{1-4}$-alkyloxycarbonyl group, an aryl-$C_{1-3}$-alkyloxycarbonyl group or a group of formula

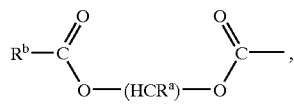

wherein $R^a$ denotes a hydrogen atom or an alkyl group and $R^b$ denotes an alkyl group or a 3- to 7-membered cycloalkyl group, even though no such compound is specifically described in this published application.

It has now been found that the phenylamidines of general formula (I)

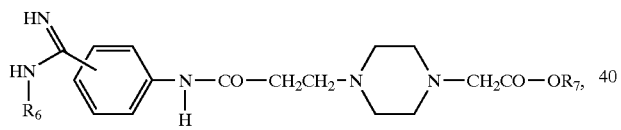

wherein $R_6$ denotes a hydroxy, $C_{1-18}$-alkyloxycarbonyl, arylcarbonyl or aryl-$C_{1-4}$-alkyloxycarbonyl group, $R_7$ denotes a hydrogen atom, a $C_{1-8}$-alkyl, $C_{4-7}$-cycloalkyl, phenyl-$C_{1-4}$-alkyl or $R_8$—CO—OCHR$_9$- group wherein $R_8$ denotes a $C_{1-4}$-alkyl, $C_{1-4}$-alkoxy, $C_{3-7}$-cycloalkyl or $C_{4-7}$-cycloalkoxy group and $R_9$ denotes a hydrogen atom or a $C_{1-4}$-alkyl group, the tautomers, the stereoisomers and the salts thereof, particularly the physiologically acceptable salts thereof with inorganic or organic acids or bases, also have valuable pharmacological properties, preferably antithrombotic effects.

The term aryl moieties mentioned in the definition of the abovementioned groups refers to a phenyl group which may in each case be monosubstituted by $R_{10}$, mono-, di- or trisubstituted by $R_{11}$ or monosubstituted by $R_{10}$ and additionally mono- or disubstituted by $R_{11}$, while the substituents may be identical or different and $R_{10}$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulphenyl, $C_{1-4}$-alkylsulphinyl, $C_{1-4}$-alkylsulphonyl, hydroxy, $C_{1-4}$-alkylsulphonyloxy, trifluoromethyloxy, nitro, amino, $C_{1-4}$-alkylamino, di-($C_{1-4}$-alkyl)-amino, $C_{1-4}$-alkylcarbonylamino, N—($C_{1-4}$-alkyl)-$C_{1-4}$-alkylcarbonylamino, $C_{1-4}$-alkylsulphonylamino, N—($C_{1-4}$-alkyl)-$C_{1-4}$-alkylsulphonylamino aminosulphonyl, $C_{1-4}$-alkylaminosulphonyl or di-($C_{1-4}$-alkyl)-aminosulphonyl group or a carbonyl group which is substituted by a 5- to 7-membered alkyleneimino group, while in the abovementioned 6- to 7-membered alkyleneimino groups a methylene group in the 4 position may in each case be replaced by an oxygen or sulphur atom or by a sulphinyl, sulphonyl, imino or N-($C_{1-4}$-alkyl)-imino group, and $R_{11}$ denotes a fluorine, chlorine, bromine or iodine atom or a $C_{1-4}$-alkyl, trifluoromethyl or $C_{1-4}$-alkoxy group or two groups $R_{11}$, if they are bound to adjacent carbon atoms, together denote a $C_{3-5}$-alkylene, methylenedioxy or 1,3-butadien-1,4-ylene group.

The present invention relates to the compounds of the above general formula I, the tautomers, the stereoisomers and the salts thereof, particularly the physiologically acceptable salts thereof with inorganic or organic acids or bases, pharmaceutical compositions containing these compounds and processes for the preparation thereof.

Preferred compounds of the above general formula I are those wherein the substituted amidino group is in the 4 position, particularly those compounds wherein $R_6$ denotes a hydroxy, $C_{1-18}$-alkyloxycarbonyl, phenylcarbonyl or phenyl-$C_{1-4}$-alkyloxycarbonyl group and $R_7$ denotes a hydrogen atom, a $C_{1-8}$-alkyl, $C_{5-7}$-cycloalkyl or phenyl-$C_{1-4}$-alkyl group, while the abovementioned phenyl moieties may in each case be mono- or disubstituted by $R_{11}$, the substituents being identical or different, and $R_{11}$ denotes a fluorine, chlorine or bromine atom, a $C_{1-2}$-alkyl, trifluoromethyl or $C_{1-2}$-alkoxy group, the tautomers, the stereoisomers and the salts thereof.

Particularly preferred compounds of the above general formula I are those wherein $R_6$ denotes a hydroxy, $C_{1-12}$-alkyloxycarbonyl, phenylcarbonyl or phenyl-$C_{1-2}$-alkyloxycarbonyl group and $R_7$ denotes a $C_{1-8}$-alkyl or $C_{5-7}$-cycloalkyl group, the tautomers, the stereoisomers and the salts thereof.

Most preferred compounds of the above general formula I are those wherein $R_6$ denotes a hydroxy, $C_{5-12}$-alkyloxycarbonyl, phenylcarbonyl or benzyloxycarbonyl group and $R_7$ denotes a $C_{1-4}$-alkyl or $C_{5-6}$-cycloalkyl group, the tautomers, the stereoisomers and the salts thereof.

The following are mentioned as examples of preferred compounds:

(1) 4-[2-[[4-(octyloxycarbonylamidino)phenyl] aminocarbonyl]-ethyl]-1-[(ethoxycarbonyl)methyl]-piperazine, (2) 4-[2-[[4-(hexyloxycarbonylamidino)phenyl] aminocarbonyl]-ethyl]-1-[(ethoxycarbonyl)methyl]-piperazine, (3) 4-[2-[[4-(methyloxycarbonylamidino)phenyl] aminocarbonyl]-ethyl]-1-[(ethoxycarbonyl)methyl]-piperazine, (4) 4-[2-[[4-(benzoylamidino)phenyl]aminocarbonyl]-ethyl]-1-[(ethoxycarbonyl)methyl]-piperazine and (5) 4-[2-[[4-(hydroxyamidino)phenyl]aminocarbonyl]-ethyl]-1-[(ethoxycarbonyl)methyl]-piperazine and the salts thereof.

The new compounds of general formula I may be obtained, for example, by the following method:
a. In order to prepare a compound of general formula I wherein
   $R_6$ has the meanings given hereinbefore, with the exception of the hydroxy group:
acylating a compound of general formula

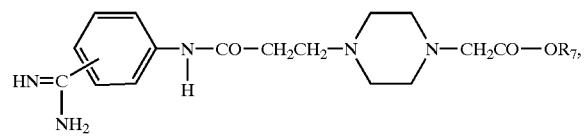

(II)

wherein
$R_7$ is as hereinbefore defined,
with a compound of general formula $Z_1-R_6'$      (III), wherein
$R_6'$ has the meanings given for $R_6$ hereinbefore, with the exception of the hydroxy group, and
$Z_1$ denotes a nucleofugic leaving group such as a halogen atom, e.g. a chlorine atom, or, if $R_6'$ denotes an arylcarbonyl group, $Z_1$ may also denote a hydroxy group.

The reaction is preferably carried out in a solvent such as acetone, methylene chloride, tetrahydrofuran, toluene, dioxane or acetonitrile, optionally in the presence of an inorganic or a tertiary organic base, preferably at temperatures between −20° C. and the boiling temperature of the solvent used.

The reaction with a compound of general formula III wherein $Z_1$ denotes a nucleofugic leaving group is preferably carried out in a solvent such as methylene chloride, acetonitrile, tetrahydrofuran, toluene, acetone or acetone/water, optionally in the presence of a base such as potassium carbonate or N-ethyl-diisopropylamine at temperatures between −10 and 60° C., and the reaction with a carboxylic acid of general formula III is preferably carried out in the presence of a dehydrating or acid-activating-agent, e.g. in the presence of isobutyl chloroformate, thionyl chloride, trimethylchlorosilane, phosphorus trichloride, N,N'-dicyclohexylcarbodiimide, N,N'-dicyclohexylcarbodiimide/N-hydroxysuccinimide, N,N'-carbonyldiimidazole or N,N'-thionyldiimidazole, triphenylphosphine/carbon tetrachloride or triphenylphosphine/diethyl azodicarboxylate, optionally in the presence of a base such as potassium carbonate, N-ethyl-diisopropylamine or N,N-dimethylamino-pyridine at temperatures between −10 and 60° C.

b. In order to prepare a compound of general formula I wherein
   $R_6$ denotes a hydroxy group:
reacting a nitrile of general formula

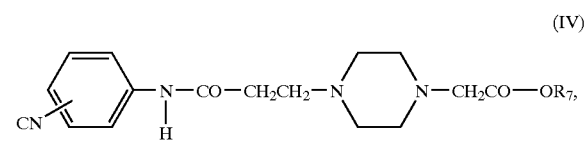

(IV)

wherein
$R_7$ is as hereinbefore defined, with hydroxylamine or the salts thereof.

The reaction is expediently carried out in a solvent such as methanol, ethanol, n-propanol, water, methanol/water, tetrahydrofuran, tetrahydrofuran/water, dioxane or dioxane/water, optionally in the presence of a tertiary organic base such as triethylamine, at temperatures between 0 and 150° C., e.g. at the boiling temperature of the reaction mixture, but preferably at temperatures between 50 and 100° C.

Moreover, the compounds of general formula I obtained may be resolved into their enantiomers and/or diastereomers and the compounds of general formula I obtained with a double bond may be resolved into their cis/trans isomers. Thus, for example, cis/trans mixtures may be resolved into their cis and trans isomers, and compounds with at least one optically active carbon atom may be resolved into their enantiomers.

Thus, for example, the cis/trans mixtures obtained may be resolved by chromatography into their cis and trans isomers, the compounds of general formula I obtained which occur as racemates may be separated into their optical enantiomers by methods known per se (cf. Allinger N. L. and Eliel E. L. in "Topics in Stereochemistry", Vol. 6, Wiley Interscience, 1971) and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds used as starting materials are known from the literature in some cases or may be obtained by methods known from the literature (see Examples).

As already mentioned, the new phenylamidines of general formula I and their salts, particularly their physiologically acceptable salts with inorganic or organic acids or bases, have valuable properties. Thus, the new phenylamidines of general formula I and their salts have valuable pharmacological properties, not only an anti-inflammatory activity and an inhibiting effect on bone degradation but also, in particular, antithrombotic and antiaggregatory effects and an inhibiting effect on tumours and metastases.

In view of their biological properties the new compounds of general formula I according to the invention and the physiologically acceptable salts thereof are suitable for treating or preventing diseases in which smaller or greater aggregations of cells occur or cell-matrix interactions play a part, e.g. in combating or preventing venous and arterial thromboses, cerebrovascular diseases, pulmonary embolism, cardiac infarct, arteriosclerosis, osteoporosis and the metastasis of tumours, and for treating genetically caused or acquired disorders of the interactions of cells with one another or with solid structures. They are also suitable as an accompanying therapy in thrombolysis using fibrinolytics or vascular interventions such as transluminal angioplasty or in the treatment of shock, psoriasis, diabetes and inflammation.

The compounds of general formula I include in particular new prodrugs of the compound
A=4-[2-[(4-amidinophenyl)aminocarbonyl]ethyl]-1-carboxymethyl-piperazine (Example 1(2) of WO 96/33970).

The biological properties of the new compounds were investigated as follows, for example:

The concentration of compound A was measured in the plasma after oral administration of the compound
B=4-[2-[[4-(hexyloxycarbonylamidino)phenyl]aminocarbonyl]-ethyl]-1-[(ethoxycarbonyl)methyl]-piperazine (Example 1(1) of the present application).

After oral administration of 1 mg/kg of compound B to Rhesus monkeys the concentration of compound A in the plasma was measured 2, 4, 8 and 24 hours after administration of the substance. For this purpose the Rhesus plasma was incubated with a suspension of human thrombocytes in plasma and the compound (3S, 5S)-5-[(4'-amidino-4-biphenylyl)-oxymethyl]-3-carboxymethyl-pyrrolidin-2-one-[3-$^3$H-4-biphenylyl] ($^3$H-BIBU 52, described in DE-A-4,214,245) as ligand. The free and bound ligand were separated by centrifugation and quantitatively determined by scintillation counting. The concentration of compound A was calculated from the amount of bound ligand using a calibration curve.

For this purpose, donor blood is taken from an anticubital vein and anticoagulated with trisodium citrate (final concentration: 13 mmol/l). The blood is centrifuged for 10 minutes at 170×g and the supernatant platelet-rich plasma (PRP) is removed. The remaining blood is sharply centrifuged off again at 3200×g and the supernatant platelet-depleted plasma (PDP) is removed.

For the calibration curve for calculating the concentration, 5 µl of a solution of compound A are added to 995 µl of PDP (final concentration 5000 nmol/l). Further plasma samples from this sample are diluted with PDP to give a final concentration of 2.5 nmol/l.

10 µl of $^3$H-BIBU 52 (final concentration 10 nmol/l), 10 µl of $^{14}$C-sucrose (370 Bq) and 80 µl of PRP are added to 150 µl of plasma sample from the Rhesus monkey or calibration curve plasma and the preparations are incubated for 20 minutes at ambient temperature. Then the samples are centrifuged for 5 minutes at 2000×g and the supernatant is drawn off. 100 µl of the supernatant are combined with 100 µl of NaOH 0.2 mol/l, 15 µl of HCl 5 mol/l and 2 ml of scintillator and the $^3$H— and $^{14}$C-radioactivity are measured quantitatively. The pellet is dissolved in 200 µl of NaOH 0.2 mol/l. 180 µl thereof are combined with 15 µl of HCl 5 mol/l and 2 ml of scintillator and the $^3$H— and $^{14}$C-radioactivity are measured. The residual plasma remaining in the pellet is determined from the $^{14}$C content and removed. The quantity of bound ligand is determined from the $^3$H content. The quantity of bound ligand is plotted against the concentration of the calibration curve plasma. The concentration of compound A in the Rhesus plasma is calculated from the quantity of bound ligand in the relevant plasma sample compared with the calibration curve.

The following Table contains the values found:

| compound | conc. of A in [nM], 2 h | conc. of A in [nM], 4 h | conc. of A in [nM], 8 h | conc. of A in [nM], 24 h |
| --- | --- | --- | --- | --- |
| B | 413 | 316 | 145 | 0 |

As the results show, after oral administration of 1 mg/kg of compound B to Rhesus monkeys, high plasma levels of the anti-thrombotically active compound A are maintained for a period of at least 8 hours.

For combating or preventing the illnesses mentioned above, the dose is between 0.1 µg and 30 mg/kg of body weight, preferably 1 µg to 15 mg/kg of body weight, administered up to 4 times a day. For this, the compounds of formula I prepared according to the invention may be formulated, optionally together with other active substances such as thromboxane-receptor antagonists and thromboxane synthesis inhibitors or combinations thereof, ADP receptor antagonists, clopidogrel, ticlopidine, serotonin antagonists, α-receptor antagonists, alkylnitrates such as glycerol trinitrate, phosphodiesterase inhibitors, prostacycline and their analogues, fibrinolytics such as tPA, prourokinase, urokinase, streptokinase, or anticoagulants such as heparin, dermatane sulphate, activated Protein C, vitamin K antagonists, hirudine, inhibitors of thrombin or other activated clotting factors, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, to produce conventional galenic preparations such as plaim or coated tablets, capsules, powders, suspensions, solutions, sprays or suppositories.

The example that follow are intended to illustrate the invention:

Preparation of the Starting Compounds:

EXAMPLE I

N-(4-cyanophenyl)-acrylamide

Prepared by reacting 4-amino-benzonitrile with acrylic acid chloride in methylene chloride in the presence of triethylamine.

Melting point: 192–194° C.

$R_f$ value: 0.43 (silica gel; methylene chloride/methanol= 20:1)

EXAMPLE II

4-[2-[(4-cyanophenyl)aminocarbonyl]ethyl]-1-[(ethoxycarbonyl)methyl]-piperazine

Prepared by reacting N-(4-cyanophenyl)-acrylamide and 1-[(ethoxycarbonyl)methyl]-piperazine in toluene at reflux temperature.

$R_f$ value: 0.80 (silica gel; methylene chloride/methanol/ conc. aqueous ammonia=9:1:0.1)

Mass spectrum: (M+H)$^+$=345

EXAMPLE III

4-[2-[(4-amidinophenyl)aminocarbonyl]ethyl]-1-[(ethoxycarbonyl)methyl]-piperazine-triacetate Prepared by catalytic hydrogenation of 4-[2-[[4-(hydroxyamidino)phenyl]-aminocarbonyl]ethyl]-1-[(ethoxycarbonyl)methyl]-piperazine in glacial acetic acid at 60° C. in the presence of palladium/charcoal.

R_f value: 0.27 (silica gel; methylene chloride/methanol/conc. aqueous ammonia=4:1:0.1)

Mass spectrum: $(M+H)^+=362$

Preparation of the End Products:

EXAMPLE 1

4-[2-[[4-(octyloxycarbonylamidino)phenyl]aminocarbonyl]-ethyl]-1-[(ethoxycarbonyl)methyl]-piperazine 6.9 g of potassium carbonate are added to 5.4 g of 4-[2-[(4-amidinophenyl)aminocarbonyl]ethyl]-1-[(ethoxycarbonyl)methyl-piperazine-triacetate in 150 ml of acetone and 50 ml of water at 0° C. To this mixture 2.9 ml of octyl chloroformate in 10 ml of acetone are added dropwise, with stirring, at a temperature below 7° C. After stirring overnight at ambient temperature the mixture is diluted with water and the acetone is drawn off in vacuo. The residue is extracted with ethyl acetate, washed with saline solution, dried and evaporated down. The residue is purified by chromatography over a silica gel column with methylene chloride/methanol, to which some concentrated aqueous ammonia has been added.

Yield: 2.3 g (45% of theory),

Melting point: 136–138° C.

R_f value: 0.27 (silica gel; methylene chloride/methanol/conc. aqueous ammonia=9:1:0.1)

The following compounds are obtained analogously to Example 1:

(1) 4-[2-[[4-(hexyloxycarbonylamidino)phenyl]aminocarbonyl]-ethyl]-1-[(ethoxycarbonyl)methyl]-piperazine Melting point: 131–134° C.

Mass spectrum: $(M+H)^+=490$ (2) 4-[2-[[4-(methoxycarbonylamidino)phenyl]aminocarbonyl]-ethyl]-1-[(ethoxycarbonyl)methyl]-piperazine Melting point: 155–156° C.

Mass spectrum: $(M+H)^+=420$ (3) 4-[2-[[4-(benzoylamidino)phenyl]aminocarbonyl]-ethyl]-1-[(ethoxycarbonyl)methyl]-piperazine Melting point: 189° C.

Mass spectrum: $(M+H)^+=466$

EXAMPLE 2

4-[2-[[4-(hydroxyamidino)phenyl]aminocarbonyl]-ethyl]-1-](ethoxycarbonyl)methyl]-piperazine To a solution of 6 g of 4-[2-[(4-cyanophenyl)aminocarbonyl]-ethyl]-1-[(ethoxycarbonyl)methyl]-piperazine in 50 ml of ethanol are added 2.4 g of hydroxylamine-hydrochloride and 4.8 ml of triethylamine and the mixture is refluxed for 3 hours. It is cooled, the precipitate is suction filtered, washed with ethanol and dried.

Yield: 5.1 g (77% of theory),

Melting point: 182–183° C.

Mass spectrum: $(M+H)^+378$

Example 3

Tablet Containing 50 mg of Active Substance

Composition

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 4

Tablet Containing 350 mg of Active Substance

Preparation

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 5

Capsules Containing 50 mg of Active Substance

Composition

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation (1) is triturated with (3). This trituration is added to the mixture of (2) and (4) with vigorous mixing.

This powder mixture is packed into size 3 hard gelatine capsules in a capsule filling machine.

EXAMPLE 6

Capsules Containing 350 mg of Active Substance

Composition

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation (1) is triturated with (3). This trituration is added to the mixture of (2) and (4) with vigorous mixing.

This powder mixture is packed into size 0 hard gelatin capsules in a capsule filling machine.

What is claimed is:

1. A compound of formula (I):

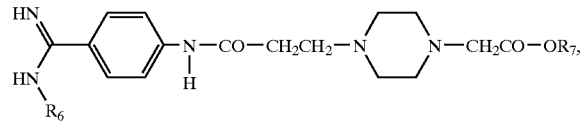

(I)

wherein
- $R_6$ denotes a hydroxy, $C_{6-12}$-alkyloxcarbonyl or, phenylcarbonyl or, and
- $R_7$ denotes $C_{1-8}$-alkyl, $C_{5-7}$-cycloalkyl or phenyl-$C_{1-4}$-alkyl group or a tautomer, stereoisomer or salt thereof.

2. A compound according to claim 1, selected from:
   (1) 4-[2-[[4-octyloxycarbonylamidino)phenyl]aminocarbonyl]-ethyl]-1-[(ethoxycarbonyl)methyl]-piperazine,
   (2) 4-[2-[[4-(hexyloxycarbonylamidino)phenyl]aminocarbonyl]-ethyl]-1-[(ethoxycarbonyl)methyl]-piperazine,
   (3) 4-[2-[[4-(benzoylamidino)phenyl]aminocarbonyl]-ethyl]-1-[(ethoxycarbonyl)methyl]-piperazine, and
   (4) 4-[2-[[4-(hydroxyamidino)phenyl]aminocarbonyl]-ethyl]-1-[(ethoxycarbonyl)methyl]-piperazine
   and the salts thereof.

3. A compound according to claim 1, selected from:
4-[2-[[4-(octyloxycarbonylamidino)phenyl]aminocarbonyl]-ethyl]-1-[(ethoxycarbonyl)methyl]-piperazine and the salts thereof.

4. A compound according to claim 1, selected from:
4-[2-[[4-(hexyloxycarbonylamidino)phenyl]aminocarbonyl]-ethyl]-1-[(ethoxycarbonyl)methyl]-piperazine and the salts thereof.

5. A physiologically acceptable salt of a compound according to claim 1 with an inorganic or organic acid or base.

6. A pharmaceutical composition comprising a compound according to claim 1 and optionally one or more inert carriers and/or diluents.

7. A pharmaceutical composition comprising a physiologically acceptable salt according to claim 5 and optionally one or more inert carriers and/or diluents.

8. A method for treating a disease or condition selected from: venous and arterial thromboses, pulmonary embolism, cardiac infarct, arteriosclerosis, comprising administering to a patient in need thereof a therapeutically effective amount of a compound according to claim 1.

* * * * *